United States Patent
Eda et al.

(10) Patent No.: US 7,873,411 B2
(45) Date of Patent: Jan. 18, 2011

(54) INTERFACE DEVICE, INTERFACE METHOD AND CONTROL TRAINING DEVICE BY THE USE OF THE INTERFACE DEVICE

(75) Inventors: Hideo Eda, Koganei (JP); Yasushi Terazono, Koganei (JP); Toshio Yanagida, Koganei (JP); Amami Kato, Suita (JP); Masayuki Hirata, Suita (JP); Masaaki Taniguchi, Suita (JP); Takahito Baba, Suita (JP); Toshiki Yoshimine, Suita (JP)

(73) Assignee: National Institute of Information and Communications Technology, Tokyo (JP)

( * ) Notice: Subject to any disclaimer, the term of this patent is extended or adjusted under 35 U.S.C. 154(b) by 1219 days.

(21) Appl. No.: 11/214,600

(22) Filed: Aug. 30, 2005

(65) Prior Publication Data

US 2006/0074822 A1 Apr. 6, 2006

(30) Foreign Application Priority Data

Sep. 1, 2004 (JP) ............................ P2004-254062

(51) Int. Cl.
*A61B 5/04* (2006.01)
(52) U.S. Cl. ....................................... 600/544; 600/545
(58) Field of Classification Search ................. 600/473, 600/475, 477, 544, 545
See application file for complete search history.

(56) References Cited

U.S. PATENT DOCUMENTS

| | | | | |
|---|---|---|---|---|
| 5,699,808 A | * | 12/1997 | John | 600/483 |
| 6,001,065 A | * | 12/1999 | DeVito | 600/544 |
| 6,533,584 B1 | * | 3/2003 | Jenkins et al. | 434/236 |
| 6,829,502 B2 | * | 12/2004 | Hong et al. | 600/544 |
| 2002/0065580 A1 | * | 5/2002 | Derakhshan | 700/245 |
| 2002/0095089 A1 | * | 7/2002 | Yamamoto et al. | 600/476 |

FOREIGN PATENT DOCUMENTS

| | | | |
|---|---|---|---|
| EP | 0 488 565 | | 6/1992 |
| JP | 63-054618 | | 3/1988 |
| JP | 09-149894 | | 6/1997 |
| JP | 10-244480 | | 9/1998 |
| JP | 2000-172407 | | 6/2000 |
| JP | 2002236096 A | * | 8/2002 |
| JP | 2002-236096 | | 12/2002 |

OTHER PUBLICATIONS

Japanese Application No. 2004-254062 Office Action "Notification of Reasons for Refusal" dated Oct. 4, 2010, 2 pages, with English translation (total of four pages).

* cited by examiner

*Primary Examiner*—Robert L Nasser
*Assistant Examiner*—Michael D'Angelo (57) ABSTRACT

An interface device in accordance with the present claimed invention is an interface device 4 that intervenes between a measuring means 2 that measures brain activities of a subject H and an object 31 to be controlled, and that comprises a reference signal storing part D1 that stores a brain activity signal measured at a time when the subject H conducts predetermined thinking different from direct thinking in order to control the object 31 to be controlled in a desired mode as a reference signal, a discriminating part 41 that compares the brain activity signal measured by the measuring means 2 with the reference signal and discriminates whether or not the thinking of the subject H is the predetermined thinking, and a controlling part 42 that controls the object 31 to be controlled in the desired mode when the discriminating part 41 discriminates that the thinking of the subject H is the predetermined thinking.

19 Claims, 8 Drawing Sheets

INTERFACE DEVICE, INTERFACE METHOD AND CONTROL TRAINING DEVICE BY THE USE OF THE INTERFACE DEVICE

BACKGROUND OF THE INVENTION AND RELATED ART STATEMENT

This invention relates to an interface device, an interface method in order to control an object to be controlled by making use of brain activities of a subject and a control training device by the use of the interface device.

Recently, researches on brain-computer interface (hereinafter called BCI) that detects nervous activities of brain and controls various devices through a computer (an interface device) have actively been conducted. In accordance with a conventional study, in order to actualize the researches, a computer (an interface device) comprehends direct thinking of a subject, for example, thinking to move to the right, by means of detecting a signal from the brain of the subject and actually controls a device to move to the right. (patent publication number 2000-172407)

A brief summary of brain researches by means of measuring brain activities will be explained below by the use of FIG. 7 wherein brain function is simplified.

Figure 7:
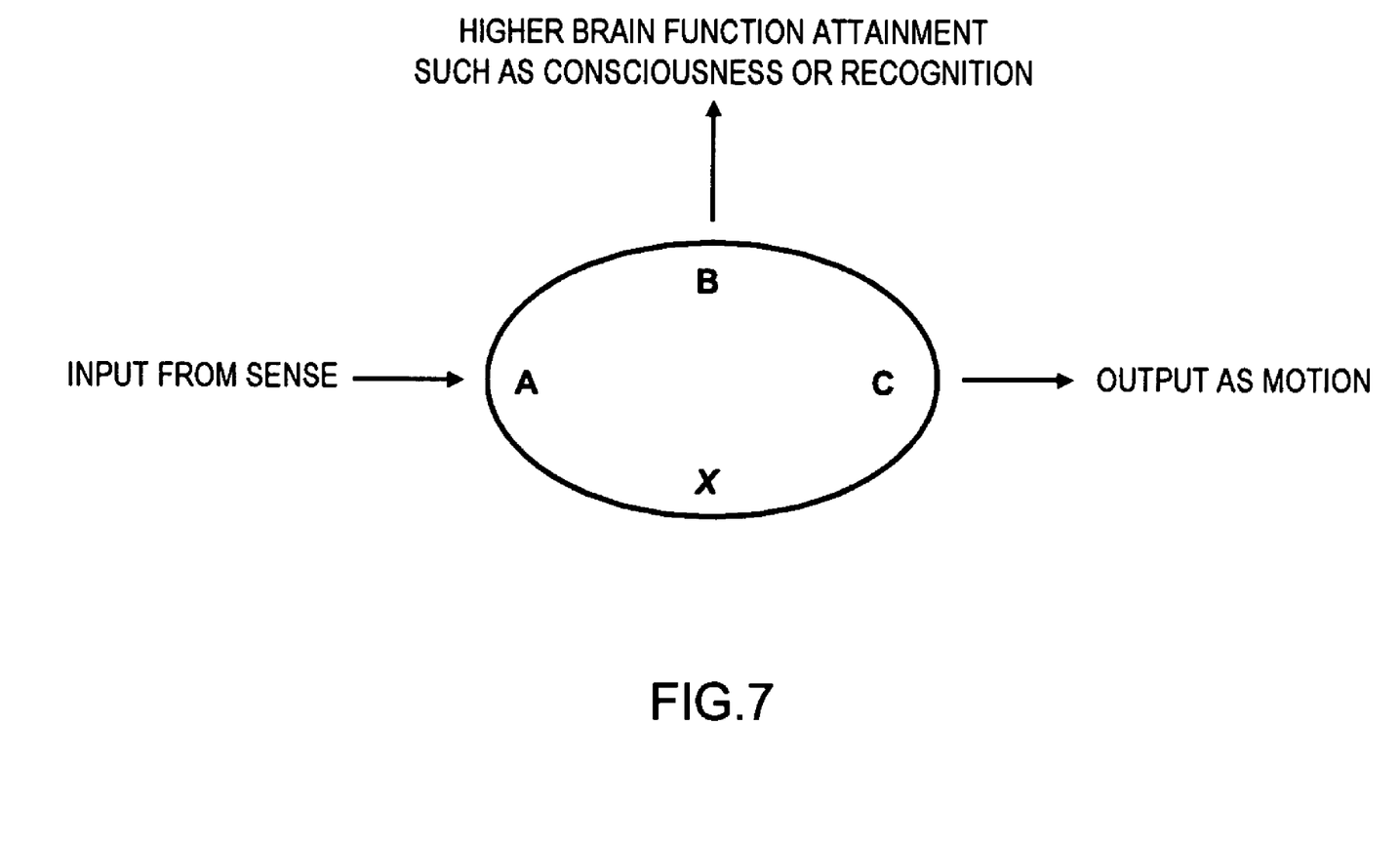
FIG. 7 is a diagram showing general brain activities and a brain pattern.

In FIG. 7, each of "A", "B" and "C" is a time and space pattern which the brain expresses respectively. This is called "representation". In order to measure the representation (practically, a part of the representation) noninvasively, there are brain activity measuring devices by the use of fMRI, near-infrared lights, MEG, EEG or ECoG (electrocorticogram).

However, it is not possible to comprehend brain activities just by the use of brain patterns measured by the brain activity measuring devices. Because there might exist unexplained "X" lying behind the brain patterns and the "X" might be an origin of each pattern or there is no knowing how many and what kind of pattern should be assumed. Furthermore, it is not easy to arrange measured data of the brain researches by means of brain activity measuring devices. Additionally, since "B" includes great variety of expressions, the brain researches are intricate.

Then take "move a wheelchair to the right" by the use of BCI for example. In case that a red button for moving the wheelchair to the right is equipped, four steps are required; (1) measure the brain, (2) interpret an intension (direct thinking) of "move to the right" based on the measured data, (3) translate the intension into a motion to push the red button, and (4) output a signal to the button. Among them, in order to interpret (2) and to translate (3), profound knowledge of brain science is required. More specifically, it is not possible comprehend how "a right direction viewed from the body", "move", or "push the red button" is expressed in the brain with consideration given to the unexplained "X". Furthermore, in measuring the brain as (1), since it is not clear which part is to be measured and how to measure, there is no choice but to measure a broader area as much as possible and as many portions as possible.

As mentioned above, an approach to comprehend direct thinking of a subject by a computer (an interface device) has no choice but to wait further developments of brain activity researches and it is a situation that an early realization of the BCI technology is difficult.

SUMMARY OF THE INVENTION

The present claimed invention changes the approach of conventional researches to a new angle or perspective wherein a subject is made to conduct direct thinking that can be comprehended by the computer (the interface device) without fail. More specifically, a desired object of the present claimed invention is to previously determine thinking that is different from direct thinking in order to control the object to be controlled in a desired mode and to control the object to be controlled in the desired mode at a time when the subject conducts the previously determined thinking.

More specifically, the interface device in accordance with the present claimed invention is an interface device that intervenes between a measuring means that measures brain activities of a subject and an object to be controlled, and is characterized by comprising a reference signal storing part that stores a brain activity signal measured at a time when the subject conducts predetermined thinking different from direct thinking in order to control the object to be controlled in a desired mode as a reference signal, a discriminating part that compares the brain activity signal measured by the measuring means with the reference signal and discriminates whether or not the thinking of the subject is the predetermined thinking, and a controlling part that controls the object to be controlled in the desired mode at a time when the discriminating part discriminates that the thinking of the subject is the predetermined thinking.

In accordance with the arrangement, it is possible to previously determine thinking that is different from direct thinking in order to control the object to be controlled in a desired mode and to control the object to be controlled in the desired mode at a time when the subject conducts the previously determined thinking. More specifically, it is possible for the subject to control the object to be controlled just by conducting the previously determined thinking if the previously determined thinking is set to be thinking that can be comprehended by a computer without fail. As a result, Brain Computer Interface technology can be actualized without intruding in a content of complicated brain activities such as, for example, reading thoughts of a subject.

In order to make it possible to control the object to be controlled in three-dimensional space, it is preferable that the predetermined thinking is six or more kinds of thinking wherein each region of a brain that becomes active at a time when the subject conducts each thinking differs mutually.

In order to make it possible for the subject to conduct the predetermined thinking, it is preferable that an image display unit to provide the subject with information is further arranged and the controlling part displays an indication on a screen to urge the subject to conduct the predetermined thinking.

In order to control the object to be controlled accurately, it is preferable that the controlling part further displays a controlling content showing a controlling signal coordinated with the reference signal on the screen.

In addition, the control training device in accordance with the present claimed invention is a control training device that comprises an interface device described wherein an image display unit to provide the subject with information is further an object to be controlled as a moving body displayed on a screen of the image display unit, and the controlling part controls the moving body.

In accordance with this arrangement, it is possible to conduct training to control the object to be controlled by conducting the predetermined thinking different from the direct thinking intending to control the object to be controlled in a desired mode. Furthermore, if training is conducted by the use of the control training device, the interface device can be appropriately used.

More concretely, it can be conceived that the moving body moves on a two-dimensional surface displayed on the screen of the image display unit or the moving body moves in three-dimensional space displayed on the screen of the image display unit.

In order to make it possible to judge whether or not the subject conducts the predetermined thinking based on an evaluation result, to see a training achievement of the subject objectively and to judge fatigue or concentration power of the subject, it is preferable that behavior of the moving body from a starting point to a destination point is set to be a parameter and an evaluating part that evaluates the parameter is provided.

As a concrete method for evaluation it can be conceived that the parameter is time until the moving body reaches the destination point from the starting point, a difference between a direct distance connecting the starting point and the destination point and a distance that the moving body actually moves, or a deviation of the moving body from a straight line connecting the starting point and the destination point.

In order to use the control training device in a state without restraining the subject, it is preferable that the measuring means irradiates near-infrared lights on the head of the subject and measures the brain activities by making use of the near-infrared spectroscopy by measuring the near-infrared lights reflected in the brain of the subject.

In accordance with the arrangement, it is possible to previously determine thinking that is different from direct thinking in order to control the object to be controlled in a desired mode and to control the object to be controlled in the desired mode at a time when the subject conducts the previously determined thinking. More specifically, it is possible for the subject to control the object to be controlled just by conducting the previously determined thinking if the previously determined think is set to be direct thinking that can be comprehended by a computer without fail. As a result, Brain Computer Interface technology can be actualized without intruding in a content of complicated brain activities such as, for example, reading thoughts of a subject.

DETAILED DESCRIPTION OF THE PREFERRED EMBODIMENTS

A control training device as one embodiment of the present claimed invention will be described below in detail with reference to the accompanying drawings.

Figure 1:
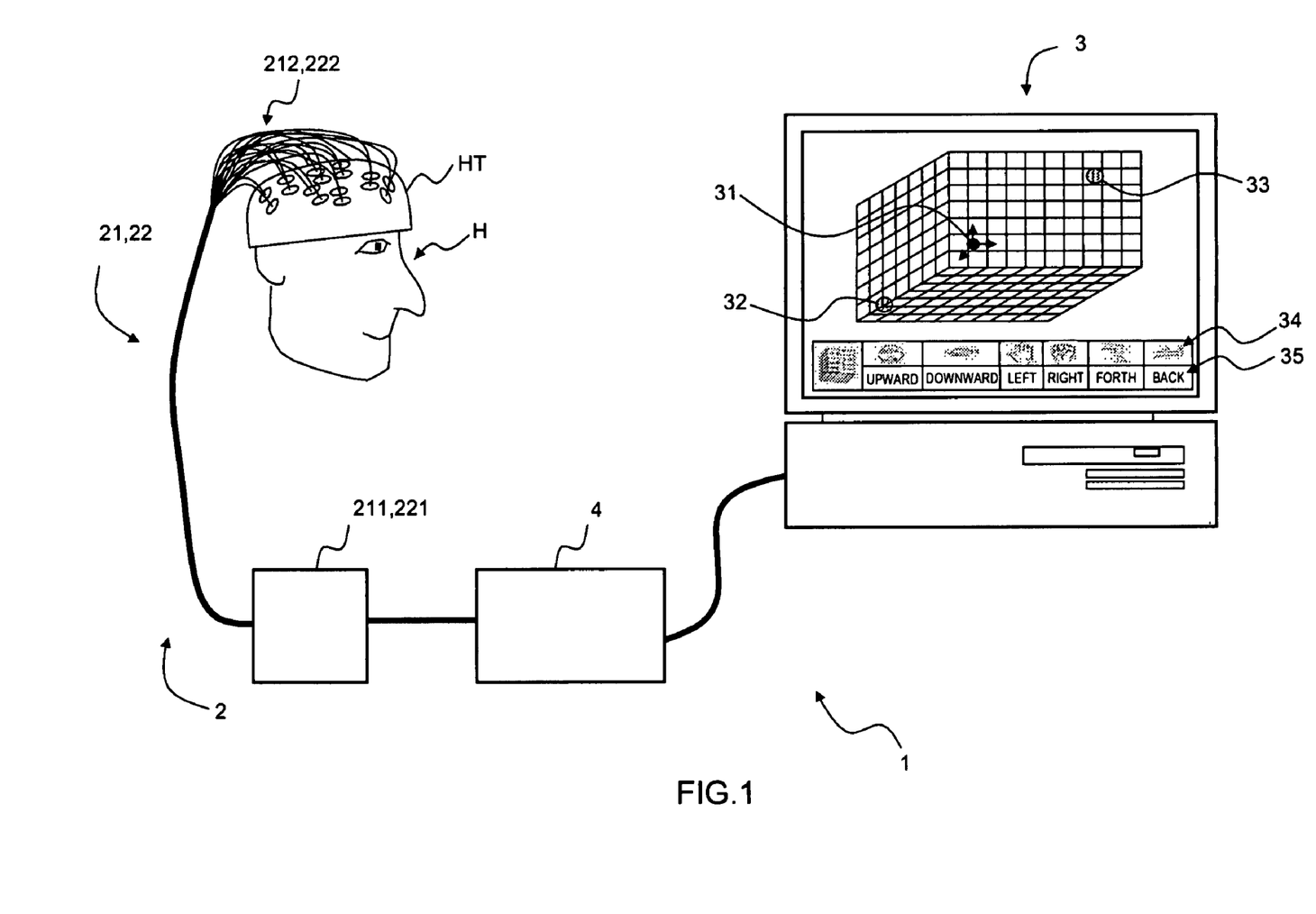
FIG. 1 is a schematic view of a pattern configuration diagram of a control training device in accordance with one embodiment of the present claimed invention.

FIG. 1 is a pattern configuration diagram showing a control training device 1 in accordance with this embodiment. The control training device 1 comprises a measuring means 2 that makes use of NIRS (near-infrared spectroscopy) that measures brain activities of a subject H, an image display unit 3 that displays three-dimensional space on its screen and displays a starting point 32, a destination point 33 and a moving body 31 as an object to be controlled in the space, and an interface device 4 that receives a brain activity signal from the measuring means 2, provides a predetermined information processing based on the brain activity signal and controls the moving body 31.

The measuring means 2, as shown in FIG. 1, has functions as a light irradiating part 21 and a light detecting part 22. The light irradiating part 21 comprises a light source 211 such as a semiconductor laser that emits near-infrared lights of multiple wavelengths (three wavelengths in this embodiment) and a flexible light guide (an optical fiber) for light transmission 212 that transmits the light emitted from the light source 211, wherein a photo derivation end of the flexible light guide for light transmission 212 is held by a head gear HT of a helmet type, a mesh type or a hair clip (a headband) type. The near-infrared lights are irradiated inside the head of the subject H when the head gear HT is mounted on the subject H.

The light detecting part 22 comprises a flexible light guide (an optical fiber) for photo acceptance 222 whose photo introduction end is held by the head gear HT, a photo acceptance element 221 such as a photomultiplier tube or a CCD element connected to a photo derivation end of the flexible light guide for photo acceptance 222, and an amplifier, not shown in drawings, wherein the near-infrared lights irradiated from the flexible light guide for light transmission 212 and scattered inside or transmitted from the head M of the subject H is introduced into the photo acceptance element 221 through the flexible light guide for photo acceptance 222 and a light intensity signal (a brain activity signal) as being an electronic signal showing its light intensity is output to the interface device 4. Each of the flexible light guide for light transmission 212 and the flexible light guide for photo acceptance 222 is singly arranged in a pair and in this embodiment multiple of pairs are arranged apart from each other and held by the head gear HT.

Figure 4:
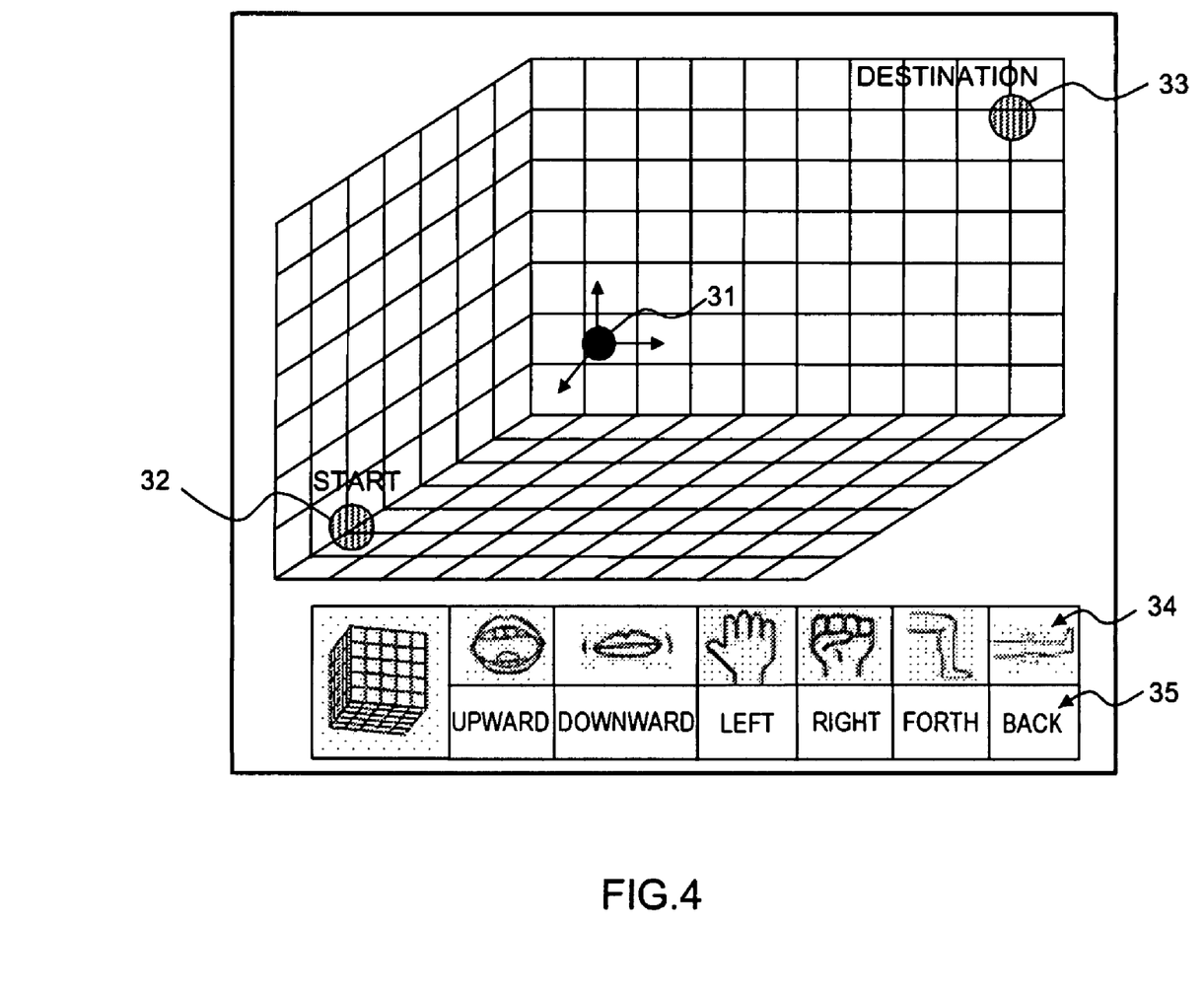
FIG. 4 is a drawing showing an indication on a screen of an image display unit in accordance with the embodiment.

The image display unit 3 displays a three dimensional space on its screen as shown in FIG. 4 and displays the starting point 32, the destination point 33 and the moving body 31 in the space. The image display unit 3 is a computer consisting of a CPU, a memory, an AD converter, an input output interface, a display and an input means.

Figure 2:
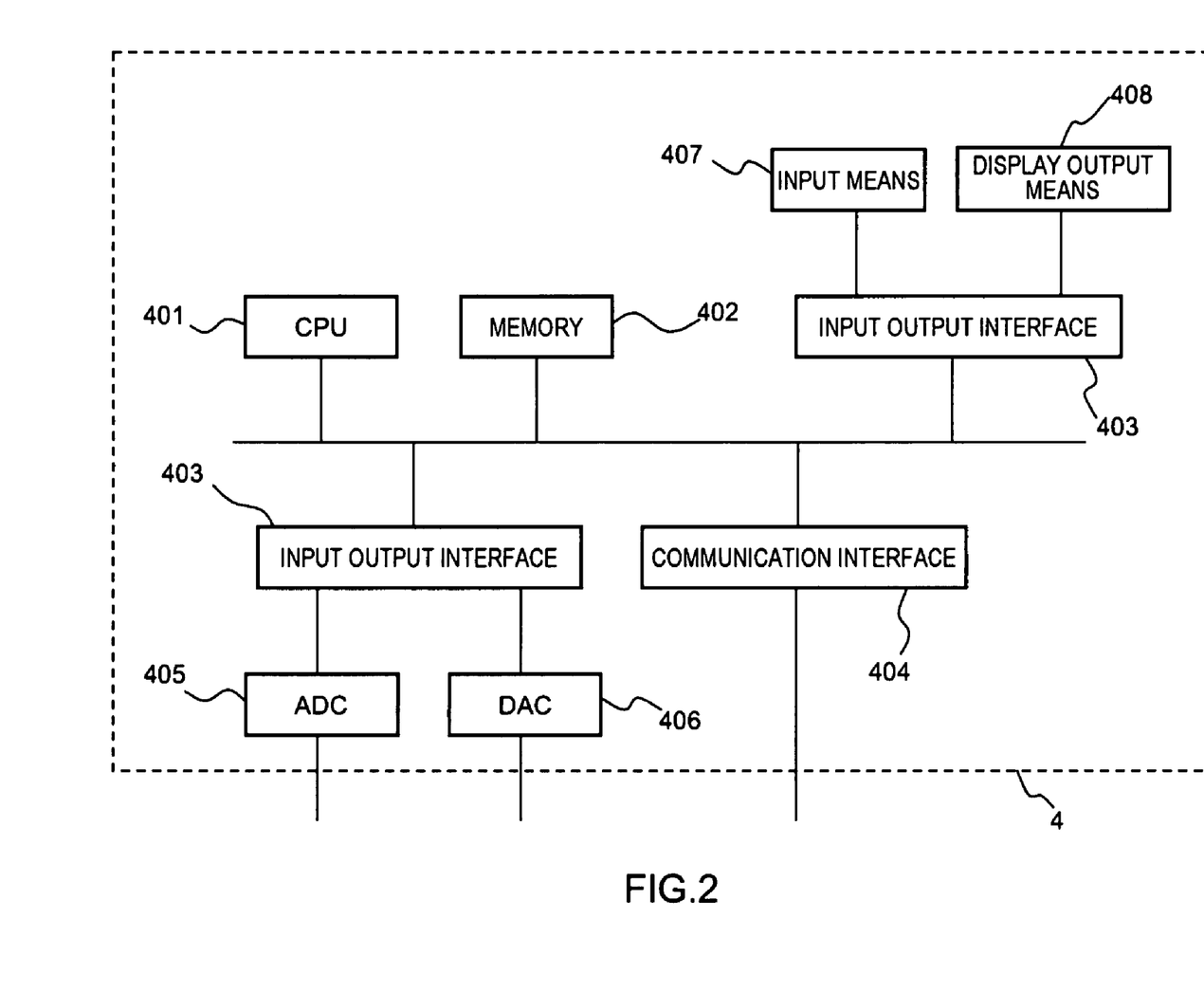
FIG. 2 is a configuration diagram showing a configuration of an interface device in accordance with the embodiment.

The interface device 4 is, as shown in FIG. 2, so called, a computer comprising a CPU 401, an involatile or volatile memory 402, an AD converter 405 or a DA converter, an input output interface 403, a display output means 408 such as a display, an input means 407 such as a mouse or a keyboard and a communication interface 404. The interface device 4 produces functions as a reference signal storing part D1, a discriminating part 41, a control signal storing part D2, a controlling part 42, an evaluating part 43 and the like, as shown by a functional block diagram in FIG. 3 in cooperation with the CPU 401 or peripheral devices based on a predetermined program memorized in the memory 402. The interface device 4 may be comprised of a single body or may be of multiple computers. It is a matter of course that a memory may be programmed with software by making use of a multipurpose computer or may be completely or partly constituted with hardware by the use of a single purpose theoretical circuit.

Each component will be concretely explained.

Figure 3:
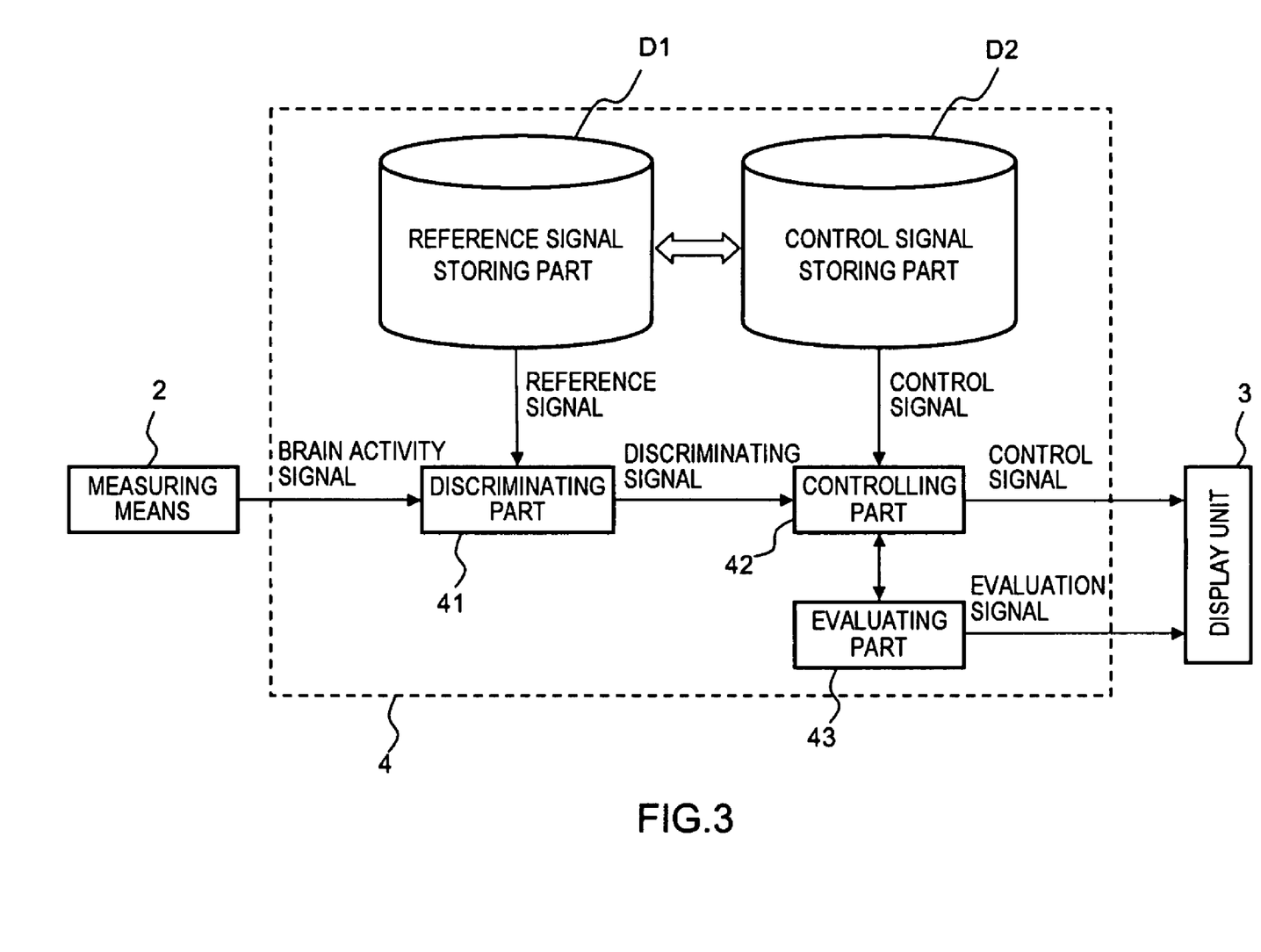
FIG. 3 is a functional block diagram showing a configuration of the interface device in accordance with the embodiment.

The reference signal storing part D1 is arranged in a predetermined area of the memory 402 and stores a brain activity signal measured by the measuring means 2 at a time when the subject H conducts predetermined thinking different from direct thinking in order to control the moving body 31 in a desired mode as a reference signal.

Figure 8:
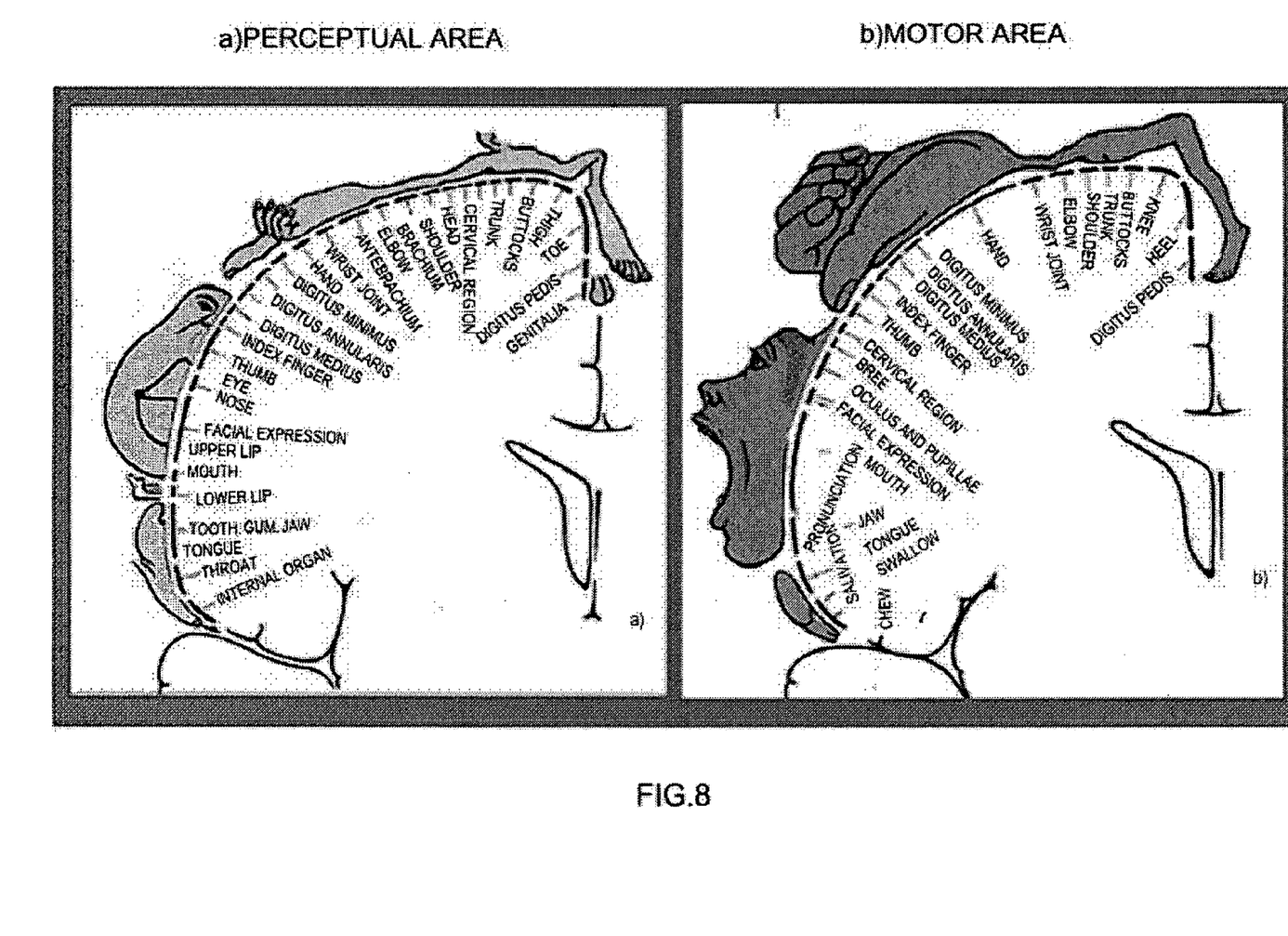
FIG. 8 is a brain functional map by means of Penfield.

The predetermined thinking is determined by the brain functional map described by Penfield as shown in FIG. 8. FIG. 8 shows a body site of which the brain is in charge regarding to both a sensorial area (described as a perceptual area in FIG. 8) and a pyramidal area. In order to make it possible for the interface device 4 to comprehend the brain activity signal without fail, select the body sites which are separated from each other as much as possible and whose proportion occupying in the brain functional map is big. More specifically, each of the body sites is, for example, a hand, a mouth or a foot. "Open a hand", "clench a hand", "open a mouth", "close a mouth", "bend a leg", "stretch a leg", or the like is set as the predetermined thinking.

The control signal storing part D2 stores a control signal for controlling the moving body 31 in a desired mode. The control signal is set to be related to each of the above-mentioned six different kinds of thinking in order to move the moving boy 31 upward and downward, right and left, and back and forth in the space. More specifically, in this embodiment, a control content of "move upward" is set to be related to "open a mouth", a control content of "move downward" is to "close a mouth", a control content of "move left" is to "open a hand", a control content of "move right" is to "clench a hand", a control content of "move forward" is to "bend a leg", and a control content of "move backward" is to "stretch a leg". In addition, accordingly, the interface device 4 outputs a control signal of 3-bit to the image display unit 3.

The discriminating part 41 receives the brain activity signal from the measuring means 2, compares the brain activity signal with the reference signal and discriminates whether or not the thinking of the subject H is the predetermined thinking.

When the discriminating part 41 discriminates that the thinking of the subject H is the predetermined thinking, the controlling part 42 controls the moving body 31 based on the control content related to the thinking. In addition, in order to make it easy for the subject H to conduct the predetermined thinking, in other words, in order to make it possible to create a brain activity pattern stably and reproductively at a time of opening or closing the mouth, opening or clenching the hand, or stretching or bending the leg, the controlling part 42 displays an indicator 34 that aids the subject H to conduct the relevant thinking on the screen of the image display unit 3, as shown in FIG. 4, and displays also the control content 35 related to the relevant thinking. The indicator 34 is not a sentence but an image showing a concrete somatoform because it is difficult for the subject H to make an image if the indicator 34 that aids the subject H to conduct the thinking is expressed by a sentence, for example, "open the mouth". It is a matter of course that the indicator 34 may be expressed by a sentence.

The evaluating part 43 judges whether or not the moving body 31 reaches the destination point 33, evaluates a behavior of the moving body 31 from the starting point 32 to the destination point 33, and outputs an evaluation signal showing an evaluation result to the image display unit 3.

A concrete method for evaluation will be described below.

As an assumption of the evaluation, a coordinate of the starting point 32 is set to be $r_s$ ($X_s$, $y_s$, $z_s$), a coordinate of the destination point 33 is set to be $r_G$($X_G$, $Y_G$, $Z_G$). The time t (s) from the starting point 32 to the destination point 33 is divided into "n" pieces, and the coordinate of the moving body 31 at each time is set to be $r_s$ ($X_s$, $y_s$, $z_s$), $r_{t1}$, ($X_{t1}$, $y_{t1}$, $z_{t1}$), $r_{t2}$ ($X_{t2}$, $y_{t2}$, $z_{t2}$), . . . .

The first evaluation method is to evaluate the time t(s) from the starting point 32 to the destination point 33. In this case, the evaluating part 43 measures the time from the starting point 32 to the destination point 33 and outputs the measured result to the image display unit 3. The subject H or an instructor can be evaluated to improve a performance of the training when the time t(s) becomes small.

The second evaluation method is that the evaluating part 43 calculates a difference d(m) between a linear distance (a direct distance)(m) connecting the starting point 32 and the destination point 33 and a distance that the moving body 31 actually moves (actually moved distance) (m).

In this case the direct distance (m) connecting the starting point 32 and the destination point 33 is $$\mathrm{sqrt}((r_G - r_s)^2)$$

where sqrt( ) is a square root of ( ).

The actually moved distance (m) that the moving body 31 moves becomes $$\mathrm{sqrt}((r_{t1}-r_s)^2) + \mathrm{sqrt}((r_{t2}-r_{t1})^2) + \ldots + \mathrm{sqrt}((r_G - r_{n-1})^2)$$

More specifically, the difference d(m) between the direct distance and the actually moved distance becomes $$d = \mathrm{sqrt}((r_{t1}-r_s)^2) + \mathrm{sqrt}((r_{t2}-r_{t1})^2) + \ldots + \mathrm{sqrt}((r_G - r_{n-1})^2) - \mathrm{sqrt}((r_G r_s)^2)$$

The evaluating part 43 calculates the difference d(m) of the distance and outputs it to the image display unit 3. The subject H or the instructor can be evaluated to improve a performance of the training when the time t(s) becomes small.

The third evaluating method evaluates a deviation s(m·m) of the moving body 31 from a straight line connecting the starting point 32 and the destination point 33.

In this case, the straight line connecting the starting point 32 and the destination point 33 is divided into "n" pieces that is the same number as that of dividing the time. Then the deviation s(m·m) from the straight line connecting the starting point 32 to the destination point 33 at each time is calculated. In other words, $$S = ((r_{t1}-r_{GS1})^2) + ((r_{t2}-r_{GS2})^2) + \ldots + ((r_m-r_{GSn})^2)$$

is calculated. Then the evaluating part 43 calculates the deviation s(m·m) and outputs it to the image display unit 3. The performance of the training of the subject H or the instructor can be evaluated by means of the deviation s(m·m).

Figure 5:
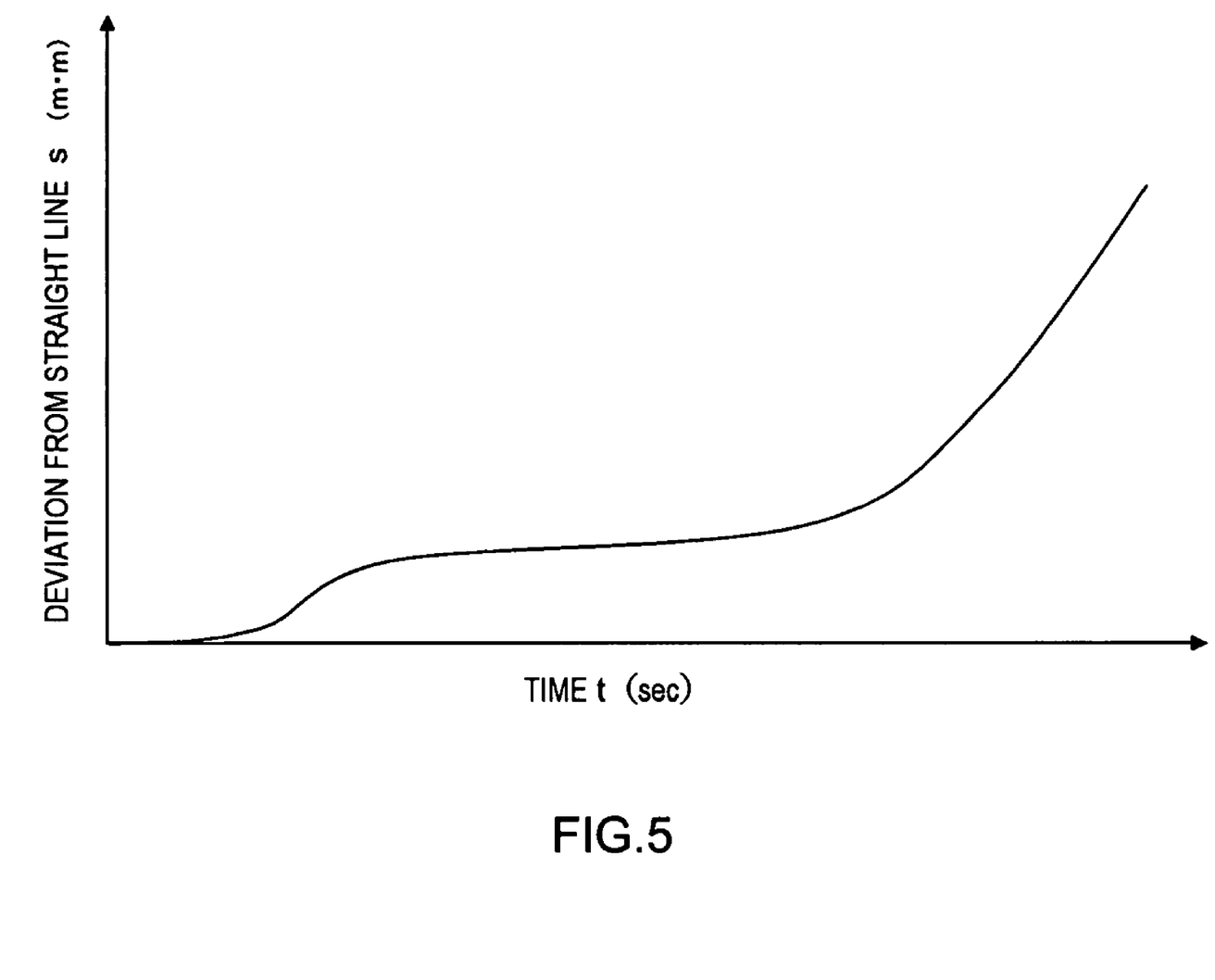
FIG. 5 is a diagram showing an evaluation result of training in accordance with the embodiment.

As a further different method for evaluation, as shown in FIG. 5, the time is denoted on the X-axis, and the difference d (m) or the deviation s(m·m) between the direct distance and the actually moved distance is denoted on the Y-axis and the evaluating part 43 outputs the time change to the image display unit 3. (The deviation s is denoted on the Y-axis in FIG. 5.) This is for the sake of making it possible for the subject H or the instructor to see achievement of the training as time-series data and to evaluate circumstance, namely, fatigue or concentration power of the subject H such that the training works out well at first but fails later during training.

Both of the difference d(m) and the deviation s(m·m) between the direct distance and the actually moved distance can be displayed at once on the Y-axis.

Figure 6:
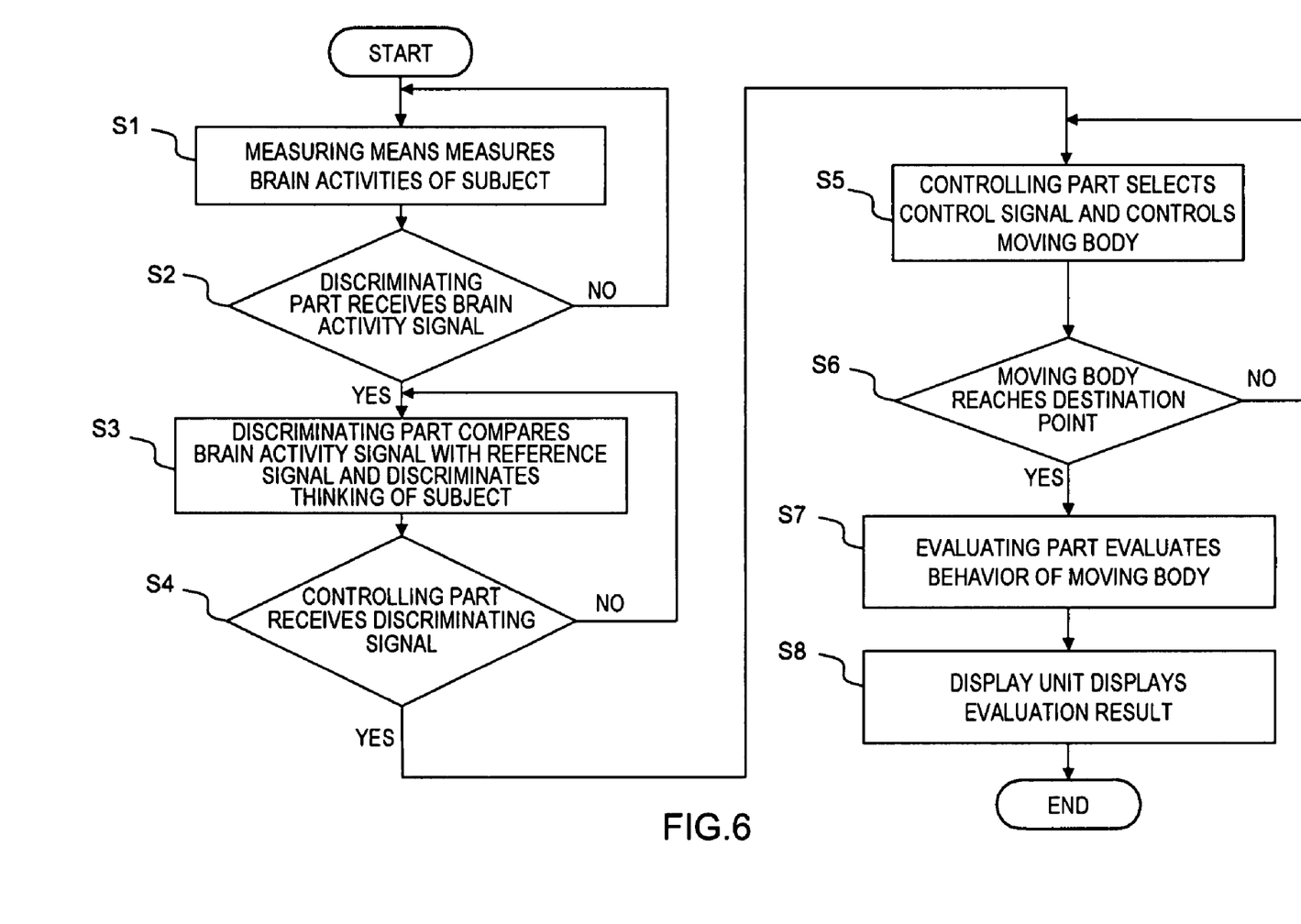
FIG. 6 is a flow chart showing a movement of the control training device in accordance with the embodiment.

Next, an operation of the control training device 1 of the above arrangement will be explained below with reference to FIG. 6.

First, the subject H conducts predetermined thinking in order to control the moving body 31 in the desired mode. Next, the measuring means 2 measures the brain activities of the subject H and outputs the brain activity signal showing its brain activities to the discriminating part 41 (step S1).

The discriminating part 41 receives the brain activity signal from the measuring means 2 (step S2), compares the brain activity signal with the reference signal that has previously been stored and discriminates the thinking of the subject H (step S3). Then the discriminating part 41 outputs a signal showing a discriminated result to the controlling part 42.

The controlling part 42 receives the signal showing the discriminated result (step S4). If the subject H conducts the predetermined thinking, the controlling part 42 selects a related controlling signal, outputs the controlling signal to the image display unit 3 and controls the moving body 31 (step S5).

If the subject H does not conduct the predetermined thinking, the controlling part 42 does not output the controlling signal. Consequently the moving body 31 does not move.

Subsequently, the evaluating part 43 judges whether or not the moving body 31 reaches the destination point 33 (step S6).

If it is judged that the moving body 31 reaches the destination point 33, the evaluating part 43 evaluates the behavior of the moving body 31 and outputs the time t(s) until the moving body 31 reaches the destination point 33, either one of the difference d(m) and the deviation s(m·m) between the direct distance and the actually moved distance, or the time series data of the difference d(m) or the deviation s (m·m) between the direct distance and the actually moved distance to the image display unit 3 (step S7). Accordingly, the image display unit 3 displays the evaluation result (step S8).

As mentioned above, in accordance with this embodiment, it is possible to give training to control the moving body 31 by conducting previously determined thinking that is different from direct thinking in order to control the moving 31 in the desired mode and that can be comprehended by the interface device 4 without fail. Accordingly, it is possible for the subject H to use the interface device 4 appropriately. As a result, the BCI technology can be actualized without intruding in a content of complicated brain activities such as, for example, reading thoughts of a subject.

Especially, since the evaluating part 43 that evaluates behavior of the moving body 31 from the starting point 32 to the destination point 33 is arranged, it is possible to appropriately judge whether or not the subject H conducts predetermined thinking based on the evaluation result. Furthermore, the achievement of the training of the subject H can be objectively judged. In addition, fatigue or concentration power of the subject H can also be judged.

Additionally, since the controlling part 42 displays the indicator to urge the subject H to conduct the predetermined thinking on the screen, it is possible to create the brain activity pattern in case of opening and closing the mouth, clenching and opening the hand, and stretching and bending the leg stably and reproducibly.

The present claimed invention is not limited to the above-described embodiment.

For example, not only data measured at the region of the brain relevant to the mouth, the hand or the leg is used without modification but also the data may be output after passing a judging means such as a neural network.

In the above-mentioned embodiment, the activity signal of the region of the brain relevant to the mouth, the hand, and the leg is used. However, it is not limited to this, and an activity signal of the region of the brain such as the Broca's area activated by language other than the mouth, the hand and the leg may be used.

The measuring means is not limited to a measuring means that makes use of NIRS (near-infrared spectroscopy), it may be FMRI (magnetic resonance imaging), MEG (magnetoencephalogram), EEG (electroencephalogram) or ECoG (electrocorticogram).

Furthermore, a number of a kind of the predetermined thinking is not limited to six as far as the interface device can comprehend the thinking without fail. Accordingly, the controlling signal that the interface device outputs to the image display unit is not limited to 3 bits.

In addition, not only the interface device is separately arranged from the image display unit, but also the interface device may be integrally arranged with the image display unit.

Furthermore, in the above-mentioned embodiment, the image display unit displays the three-dimensional space, however, the image display unit may display a plane surface on which the moving body, the starting point and the destination point are displayed.

In addition, in the above-mentioned embodiment, the controlling contents are "move upward", "move downward", "right", "move left", "move forward", and "move backward". However, if other desired controlling content is coordinated with the object to be controlled, various different kinds of control can be conducted.

Furthermore, an obstacle may be arranged between the starting point and the destination point. In addition, a path along which the moving body is to move may be determined in advance and a track along which the moving body actually moves based on the path may be evaluated. The present claimed invention may be variously modified without departing from the spirit of the invention.

The invention claimed is:

1. An interface device intervening between a measuring unit that measures brain activities of a subject and an object to be controlled, and comprising:
   a reference signal storing part that stores a brain activity signal measured at a time when the subject conducts predetermined thinking which causes movement of the object and is different from direct thinking in order to control the object to be controlled in a desired mode as a reference signal, wherein the predetermined thinking is multiple kinds of thinking about movements of body sites, the predetermined thinking is conducted in regions of the subject's brain corresponding to areas in a Penfield's brain functional map representative of portions of the brain that are separate from each other and correspond to the body sites,
   a discriminating part that compares the brain activity signal measured by the measuring unit with the reference signal and discriminates whether or not the thinking of the subject is the predetermined thinking,
   a controlling part that controls the object to be controlled in the desired mode at a time when the discriminating part discriminates that the thinking of the subject is the predetermined thinking, and
   an image display unit to provide the subject with predetermined information that is arranged on the image display unit, wherein the controlling part displays an indication on a screen to aid the subject in conducting the predetermined thinking when the object is being controlled and a control content related to the predetermined thinking, wherein the indication is an image showing movements of the body sites.

2. The interface device described in claim 1, wherein the predetermined thinking is six or more kinds of thinking wherein each region of a brain that becomes active at a time when the subject conducts each thinking differs mutually.

3. The interface device described in claim 1, wherein the controlling part further displays a controlling content of the desired mode on the screen.

4. The interface device described in claim 1, further comprising an image display unit to provide the subject with information, wherein the object to be controlled is a moving body displayed on a screen of the image display unit, and wherein the controlling part controls the moving body.

5. The interface device described in claim 4, wherein the moving body moves on a two-dimensional surface displayed on the screen of the image display unit.

6. The interface device described in claim 4, wherein the moving body moves in three-dimensional space displayed on the screen of the image display unit.

7. The interface device described in claim 4, wherein behavior of the moving body from a starting point to a destination point is set to be a parameter and an evaluating part that evaluates the parameter is provided.

8. The interface device described in claim 7, wherein the parameter is time until the moving body reaches the destination point from the starting point.

9. The interface device described in claim 7, wherein the parameter is a difference between a direct distance connecting the starting point and the destination point and a distance that the moving body actually moves.

10. The interface device described in claim 7, wherein the parameter is a deviation of the moving body from a straight line connecting the starting point and the destination point.

11. The interface device described in claim 4, wherein the measuring unit irradiates near-infrared lights on the head of the subject and measures the brain activities by making use of the near-infrared spectroscopy by measuring the near-infrared lights reflected in the brain of the subject.

12. The interface device described in claim 1, wherein the predetermined thinking includes a set of predetermined thoughts corresponding to a set of predetermined object movements.

13. The interface device described in claim 12, wherein the set of predetermined thoughts includes one of thinking of opening a hand, clenching the hand, opening a mouth, closing the mouth, bending a leg, and stretching the leg.

14. The interface device described in claim 12, wherein the set of predetermined thoughts comprise more than two thoughts.

15. The interface device described in claim 12, wherein the set of predetermined object movements comprise moving upward, moving downward, moving to the left, moving to the right, moving forward, and moving backward.

16. The interface device described in claim 1, wherein the predetermined thinking creates the brain activity signal to enable physical movement of the subject.

17. A control training device comprising:
a measuring unit that measures brain activities of a subject, the measuring unit positioned to measure regions of the subject's brain that conduct predetermined thinking, the predetermined thinking is multiple kinds of thinking about movements of body sites, the regions of the subject's brain corresponding to areas in a Penfield's brain functional map representative of portions of the brain that are separate from each other and correspond to the body sites,
an interface device intervening between the measuring unit and an object to be controlled, the interface device comprising:
a reference signal storing part that stores a brain activity signal measured by the measuring unit, measured at a time when the subject conducts the predetermined thinking which causes movement of the object and is different from direct thinking in order to control the object to be controlled in a desired mode as a reference signal,
a discriminating part that compares the brain activity signal measured by the measuring unit with the reference signal and discriminates whether or not the thinking of the subject is the predetermined thinking,
a controlling part that controls the object to be controlled in the desired mode at a time when the discriminating part discriminates that the thinking of the subject is the predetermined thinking, and
an image display unit to provide the subject with information, wherein
the image display unit displays an indication to aid the subject to conduct the predetermined thinking when the object is being controlled and a control content related to the predetermined thinking, wherein the indication is an image showing movements of the body sites, wherein
the object to be controlled is a moving body displayed on a screen of the image display unit and
the controlling part controls the moving body.

18. An interface method intervening between a measuring unit that measures brain activities of a subject and an object to be controlled, and comprising:
a step to store a brain activity signal measured at a time when the subject conducts predetermined thinking which causes movement of the object and is different from direct thinking in order to control the object to be controlled in a desired mode as a reference signal, wherein the predetermined thinking is multiple kinds of thinking about movements of body sites, the predetermined thinking is conducted in regions of the subject's brain corresponding to areas in a brain functional map representative of portions of the brain that are separate from each other and correspond to the body sites,
a discriminating step to compare the brain activity signal measured by the measuring unit with the reference signal and to discriminate whether or not the thinking of the subject is the predetermined thinking,
a controlling step to control the object to be controlled in the desired mode at a time when the discriminating step discriminates that the thinking of the subject is the predetermined thinking,
an image displaying step to provide the subject with information and an indication to aid the subject to conduct the predetermined thinking when the object is being controlled and a control content related to the predetermined thinking, wherein the indication is an image showing movements of the body sites.

19. A control training device comprising:
a measuring unit that measures brain activities of a subject, the measuring unit positioned to measure regions of the subject's brain that conduct predetermined thinking, each of the regions of the brain differing mutually and controlling movement of a body site, one of the regions of the brain conducting at least two kinds of predetermined thinking, each kind of predetermined thinking being related to a movement of the body site, a reference signal storing part that stores a brain activity signal measured by the measuring unit that corresponds to the one of the regions of the brain, the brain activity signal measured at a time when the subject conducts one of the at least two kinds of predetermined thinking which causes movement of an object to be controlled and is different from direct thinking in order to control the object in a desired mode as a reference signal, a discriminating part that compares the brain activity signal measured by the measuring unit with the reference signal and discriminates whether or not the thinking of the subject is the one of the at least two kinds of predetermined thinking, and a controlling part that controls the object in the desired mode at a time when the discriminating part discriminates that the thinking of the subject is the one of the at least two kinds of predetermined thinking, an image display part that provides the subject with information that is arranged on the image display part and that the controlling part displays an indication on a screen to aid the subject to conduct the predetermined thinking when the object is being controlled and a control content related to the predetermined thinking, wherein the indication is an image showing movements of the body site.

* * * * *